United States Patent [19]

Linn et al.

[11] Patent Number: 4,873,224
[45] Date of Patent: Oct. 10, 1989

[54] AVERMECTIN DERIVATIVES

[75] Inventors: Bruce O. Linn, Bridgewater; Helmut Mrozik, Matawan, both of N.J.

[73] Assignee: Merck & Co., Inc., Rahway, N.J.

[21] Appl. No.: 197,731

[22] Filed: May 23, 1988

[51] Int. Cl.$^4$ .................. A61K 31/70; C07H 17/08
[52] U.S. Cl. .................................. 514/30; 536/7.1
[58] Field of Search ........................ 536/7.1; 514/30

[56] References Cited

U.S. PATENT DOCUMENTS 4,378,353  3/1983  Goegelman et al. .............. 536/7.1

OTHER PUBLICATIONS

Morrison et al., *Organic Chemistry*, 3rd ed., (1973) pp. 740–741.

*Primary Examiner*—Johnnie R. Brown
*Assistant Examiner*—Elli Peselev
*Attorney, Agent, or Firm*—David L. Rose; Hesna J. Pfeiffer

[57] ABSTRACT

There are disclosed novel avermectin compounds wherein the 4″ or 4′ hydroxy group is oxidized to an oxo group and replaced with a semicarbazone, carbonyl- or sulfonyl- hydrazone, hydrazone, or oxime, and optionally reduced to the corresponding semicarbazide, carbonyl- or sulfonyl-hydrazide or hydrazine. The semicarbozones and hydrazones are prepared from the 4″ or 4′ oxo compound using the corresponding semicarbazides or hydrazines. The compounds have utility as anti-parasitic agents and compounds for that use are also disclosed. The compounds are also highly potent insecticides against agricultural pests. Compositions for such uses are also disclosed.

13 Claims, No Drawings

AVERMECTIN DERIVATIVES

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted thereon at the 13-position with a 4-($\alpha$-L-oleandrosyl)-$\alpha$-L-oleandrose group. The avermectin compounds and the instant derivatives thereof have a very high degree of anthelmintic and anti-parasitic activity.

The avermectin series of compounds isolated from the fermentation broth have the following structures:

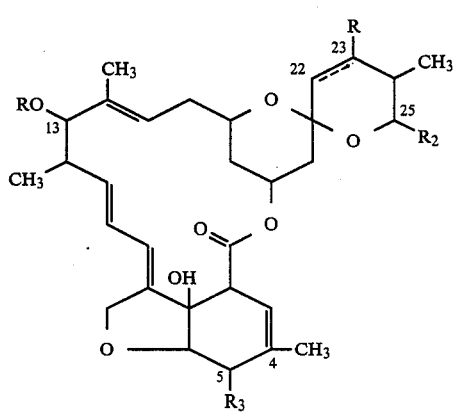

wherein R is the 4'-($\alpha$-1-oleandrosy)-$\alpha$-1-oleandrose group of the structure:

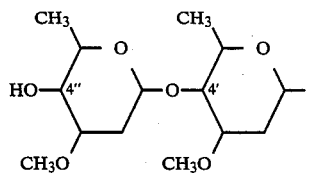

and wherein the broken line indicates a single or a double bond;

$R_1$ is hydrogen or hydroxy and is present only when said broken line indicates a signal bond;

$R_2$ is iso-propyl or sec-butyl; and $R_3$ is methoxy or hydroxy.

There are eight different avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below. (The R group is 4'($\alpha$-L oleandrosyl)-$\alpha$-L-oleandrose):

|     | $R_1$ | $R_2$ | $R_3$ |
| --- | --- | --- | --- |
| A1a | (22,23-Double Bond) | sec-butyl | —OCH$_3$ |
| A1b | (22,23-Double Bond) | iso-propyl | —OCH$_3$ |
| A2a | —OH | sec-butyl | —OCH$_3$ |
| A2B | —OH | iso-propyl | —OCH$_3$ |
| B1a | (22,23-Double Bond) | sec-butyl | —OH |
| B1b | (22,23-Double Bond) | iso-propyl | —OH |
| B2a | —OH | sec-butyl | —OH |
| B2b | —OH | iso-propyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

The terminal hydroxy group of the 13-position disaccharide substituent is situated at what is referred to as the 4''-position. In U.S. Pat. No. 4,427,663 to Mrozik, certain 4'' derivatives of avermectin compounds are discussed, specifically 4''-amino compounds. Amino and alkyl amino derivatives at the 4''-position are disclosed however the semicarbazones and hydrazones of the instant invention are not suggested.

SUMMARY OF THE INVENTION

The instant invention is concerned with certain derivatives of avermectin compounds wherein the 4''-hydroxy group is oxidized to ketone and replaced by a semicarbazone, carbonyl or sulfonyl-hydrazone, hydrazone or oxime and optionally reduced to the corresponding semicarbazide, carbonyl- or sulfonyl- hydrazide or hydrazine. Thus it is an object of the instant invention to describe such 4''-substituted avermectin compounds. A further object is to describe processes for the preparation of such compounds. A still further object is to describe the uses of such compounds as anti parasitic agents and anti bacterial agents. Still further objects will become apparent from a reading of the following description.

DESCRIPTION OF THE INVENTION

The compounds of the instant invention have the following structural formula.

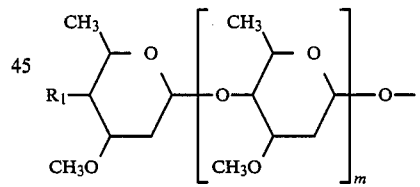

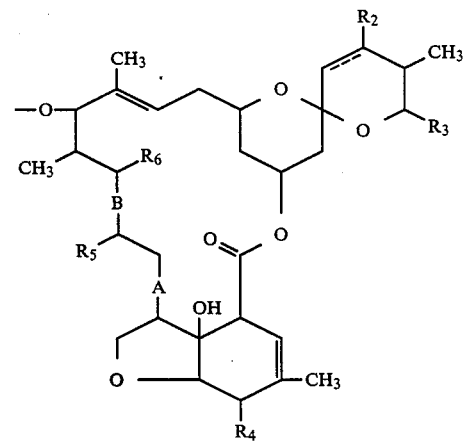

wherein
m is 0 or 1;
$R_1$ is

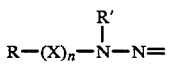

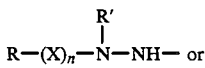

wherein
n is 0 or 1;

R is hydrogen, amino, loweralkyl, mono- or di-lower alkyl amino, methoxy-loweralkylamino, diloweralkylamino-loweralkylamino, diloweralkylamino-loweralkylamino, loweralkylphenyl, loweralkyl phenylamino, loweralkoxyphenyl, loweralkoxyphenylamino, halophenyl, halophenylamino, sulfamylphenyl, sulfamylphenylamino, morpholinyl, N-loweralkyl piperazinyl, N-(loweralkoxy-phenyl) piperazinyl, N-(halophenyl)-piperazinyl, benzimidazolylamino, pyrimidinylamino, thiazolylamino, benzothiazolyamino, or N (loweralkylphenyl)piperazinyl;

R' is hydrogen or loweralkyl;
X is carbonyl or sulfonyl;
A is a double bond or an epoxide;
B is a single bond or a double bond;
$R_2$ is hydrogen or hydroxy,
$R_3$ is iso-propyl or sec butyl,
$R_4$ is hydroxy or methoxy,
$R_5$ and $R_6$ are present only when B is a single bond and are independently hydrogen, hydroxy or halogen;
and the broken line indicates a single or a double bond at the 22,23-position, provided that $R_2$ is hydroxy only when the broken line indicates a single bond.

The term "loweralkyl" when used in the instant application is intended to represent those alkyl groups either straight or branched chain which have from 1 to 5 carbon atoms. Examples of such alkyl groups are methyl, ethyl, propyl, iso propyl, butyl, sec-butyl, pentyl, and the like.

The term "loweralkoxy" is intended to include those alkoxy groups of from 1 to 5 carbon atoms in either a straight or branched chain examples of such alkoxy groups are methoxy, ethoxy, propoxy, butoxy, pentoxy, isopentoxy and the like.

The term "loweralkanoyl" is intended to include those alkanoyl groups containing from 1 to 5 carbon atoms in either a straight or branched chain. Examples of such alkanoyl groups are formyl, acetyl, propionyl, butyryl, valeryl, and the like.

The term "halogen" is intended to include those halogen atoms fluorine, chlorine, bromine and iodine.

One aspect of the preferred compounds of this invention is realized in the above structural formula when
m is 1,
$R_1$ is

and R is amino, loweralkyl, mono- or di lower alkyl amino, methoxyloweralkylamino, diloweralkylaminoloweralkylamino, loweralkylphenyl, loweralkyl phenylamino, halophenyl, halophenyl amino, morpholinyl, N-loweralkyl piperazinyl, N-(loweralkoxyphenyl)piperazinyl, N-(halophenyl)piperazinyl, or N-(loweralkylphenyl)piperazinyl;
or $R_1$ is —NH—NRR' and R is loweralkyl, methoxyloweralkyl, diloweralkylaminoloweralkyl, loweralkylphenyl, halophenyl, morpholinyl, carbonyl, N-loweralkyl piperazinyl carbonyl, M-(loweralkylphenyl)piperazinylcarbonyl;

R' is hydrogen or loweralkyl;
A is a double bond;
B is a single bond or a double bond;
$R_2$ is hydrogen
$R_3$ is iso-propyl or sec-butyl or sec-butyl,
$R_4$ is hydroxy
$R_5$ and $R_6$ are present only when B is a single bond and are independently hydrogen or fluorine;
and the broken line indicates a single or a double bond at the 22,23-position.

Further examples of preferred compounds of the instant invention are wherein M=1,
$R_1$ is

and R is mono- or di lower alkyl amino, diloweralkylaminoloweralkylamino, loweralkylphenyl, halophenyl, N-loweralkyl piperazinyl, and N-(loweralkylphenyl)piperazinyl or $R_1$ is

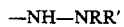

and R is loweralkyl, or N-(loweralkylphenyl)-piperazinyl carbonyl
R' is hydrogen or loweralkyl;
A is a double bond;
B is a double bond;
$R_2$ is hydrogen
$R_3$ is iso propyl or sec-butyl,
$R_4$ is hydroxy,
$R_5$ and $R_6$ are hydrogen;
and the broken line indicates a single or a double bond at the 22,23-position.

Preferred compounds of the instant invention are realized in the following specific compounds 4''-Oxoavermectin B1a/1b 4,4-dimethylsemicarbazone 4''-Oxoavermectin B1a/B1b semicarbazone 4'-Oxoavermectin B1a/B1b monosaccharide 4 methylsemicarbazone 2,23-Dihydro-4''-oxo avermectin B1a/B1b semicarbazone 10,11-Dihydro-10-fluoro 4''-oxoavermectin B1a/B1b semicarbazone 10,11-Dihydro-4''oxoavermectin B1a/B1b semicarbazone 10,11-Dihydro-10-fluoro 4''-oxoavermectin B1a/B1b 4,4-dimethylsemicarbazone 4''-Oxoavermectin B1a/1b 2-[(morpholin-4-yl)carbonyl]hydrazone 4''-Oxoavermectin B1a/1b 4 (1H-benzimidazol-2-yl)semicarbazone 4''-Oxoavermectin B1a/1b 4 (thiazol-2-yl)semicarbazone 4''-Oxoavermectin B1a/1b 4-(benzothiazol 2-yl)semicarbazone 4″-Oxoavermectin B1a/1b 4-(pyrimidin-2-yl)semicarbazone
4″-Oxoavermectin B1a/1b 4(4-chlorophenyl)semicarbazone
4″-Oxoavermectin B1a/1b 2-[(4-methylpiperazin 1-yl)carbonyl]hydrazone
4″-Oxoavermectin B1a/1b 2-[(4-ethylpiperazin-1-yl)carbonyl]hydrazone
4″-Oxoavermectin B1a/1b 2-{[4-(isopropylaminocarbonylmethyl)piperazin 1-yl]carbonyl}hydrazone
4″-Oxoavermectin B1a/1b 2-{[4-(4-chlorophenyl)piperazin-1-yl)carbonyl}hydrazone
4″-Oxoavermectin B1a/1b 2-{[4-(4-tolyl)piperazin-1-yl]carbonyl}hydrazone
22,23-Dihydro-4″-oxoavermectin B1a/1b 2-{[4-(4-tolyl)piperazin 1-yl]carbonyl}hydrazone
4″-Oxoavermectin B1a/1b 2-{[4-(4-methoxyphenylpiperazin-1-yl)carbonyl}hydrazone
4″-Oxoavermectin B1a/1b 4-(2-dimethylaminoethyl)-semicarbazone.
4″-Oxoavermectin B1a/1b 4-(2-methoxyethyl)semicarbazone.
4″-Oxoavermectin B1a/1b p-toluic acid hydrazone
4″-Oxoavermectin B1a/1b p-chlorobenzoic acid hydrazone
10,11 Dihydro 10-fluoro-4″-oxoavermectin B1a/B1b p-toluic acid hydrazone
4″-Oxoavermectin B1a/1b-acethydrazone
4″-Oxoavermectin B1a/1b-methylsulfonylhydrazone
4″Oxoavermectin B1a/1b p-toluenesulfonylhydrazone
10,11-Dihydro-10-fluoro 4″-oxoavermectin B1a/B1b p-toluenesulfonylhydrazone
4″-(Semicarbazide-1-yl)-4″-deoxyavermectin B1a/1b
4″-epi-(Semicarbazide-1-yl)-4″-deoxyavermectin B1a/1b
4″-epi-(4-Methylsemicarbazid-1-yl) 4″-deoxyavermectin B1a/1b
4″-[2-(p-Toluic acid)hydrazid-1-yl]4″-deoxyavermectin B1a/1b
4″-[2-(Toluenesulfonyl)hydrazid-1-yl]4″-deoxyavermectin B1a/1b
4″-epi-(2,2-Dimethylhydrazin-1-yl)-4″-deoxyavermectin
4″-(2,2-Dimethylhydrazin-1-yl)-4″-deoxyavermectin B1a/1b
22,23-Dihydro-4″-epi-(2,2-dimethylhydrazin-1-yl)-4″-deoxyavermectin B1a/1b
22,23-Dihydro-4′-epi (2,2-dimethylhydrazin-1-yl)-4′-deoxyavermectin B1a/1b monosaccharide
10,11 Dihydro-4″-epi-(2,2-dimethylhydrazin 1-yl)-4″-deoxy-10-fluoroavermectin b1a/1b
4″-epi (Morpholin-4-yl)amino-4″-deoxyavermectin B1a/1b
4″-Oxoavermectin B1a/B1b methoxime The “b” compounds, those with a 25-iso-propyl group, may be somewhat difficult to separate from the corresponding “a” compound with a 25-sec butyl group and as such the compounds are generally isolated as mixtures of the two compounds. Thus references in the instant application to “a” compounds such as B1a, A1a, and the like, are construed to actually contain a certain proportion of the corresponding “b” compound. Alternatively, this representation of a mixture is sometimes done by referring to the B1 or B2 compounds without specifically designating “a” or “b” compounds, or by separating the “a” compound from the “b” compound by a slash (/) such as B1a/B1b, B2a/B2b and the like.

The compounds of the instant invention are prepared using the procedures exemplified in the following reaction scheme:

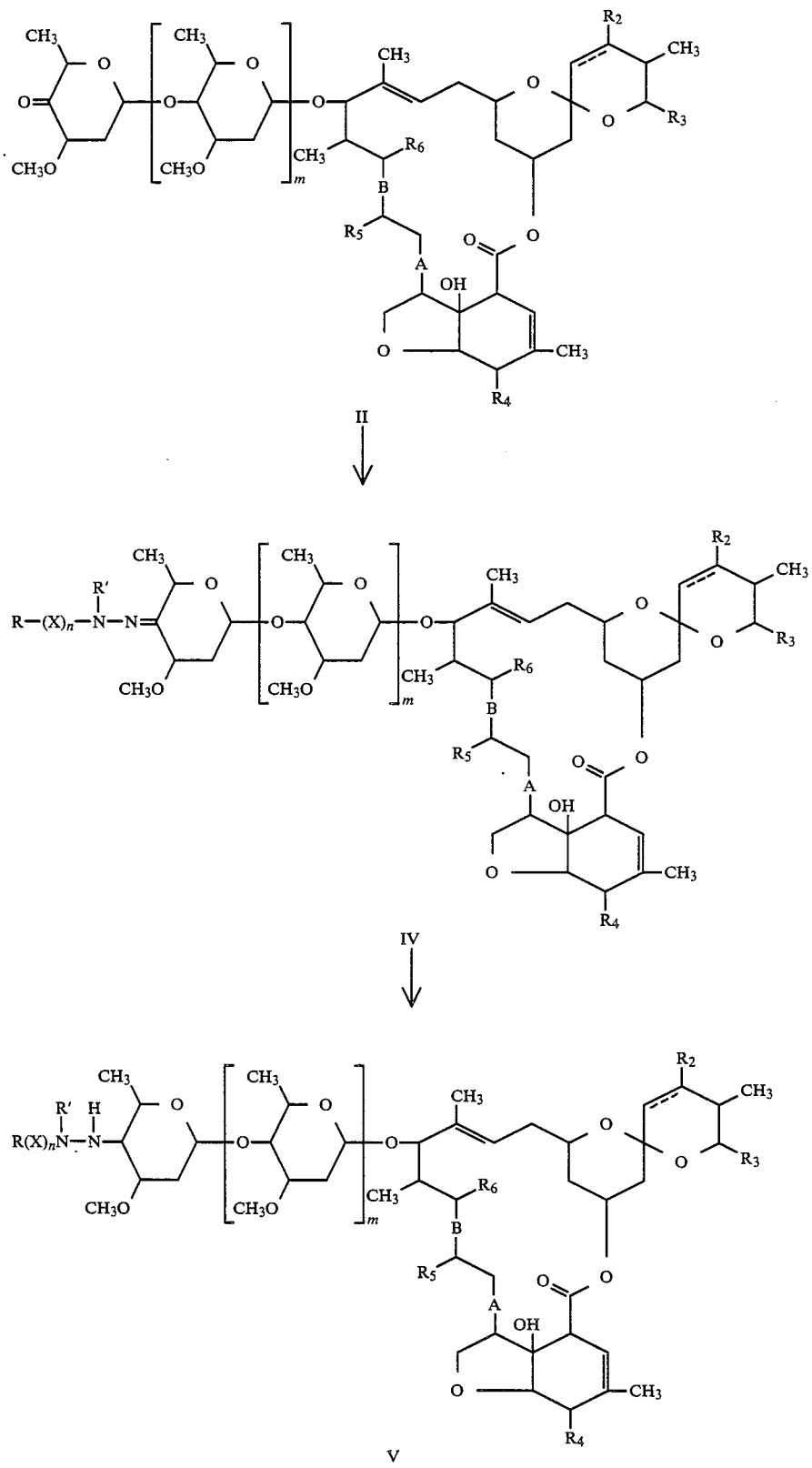

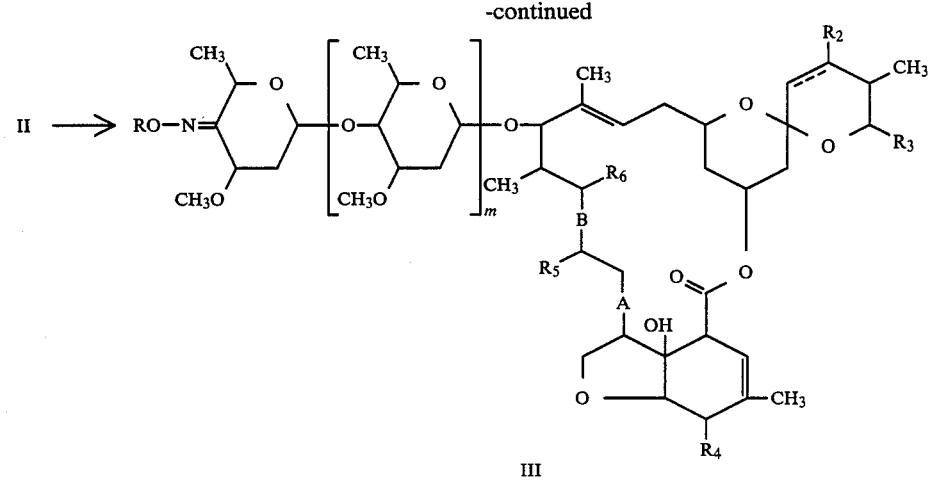

III wherein m, R, R , X, A, B, $R_2$, $R_3$, $R_4$, $R_5$ and $R_6$ are as previously defined.

In the first step of the foregoing reaction scheme, the avermectin starting materials (I) which may be either the naturally occurring products, the 22,23-dihydro derivatives thereof or the monosaccharide derivative thereof, are oxidized at the 4″-position (or 4′position) to the corresponding keto compound (compound II). During the procedure the presence of any hydroxy groups at the 5 and 23-positions will require that such hydroxy groups be protected in order that they too are not oxidized. The 7-hydroxy group is very non reactive and inert to such reaction conditions and need not be protected. The procedure used to prepare the protected intermediates are described below. The oxidation reaction is carried out in an inert solvent such as methylene chloride using oxalyl chloride or trifluoroacetic anhydride and dimethylsulfoxide as the oxidizing agent. Additionally N-chlorosuccinimide and dimethylsulfide may be employed. The reaction proceeds by dissolving the oxalyl chloride or trifluoroacetic anhydride and dimethylsulfoxide (or other oxidizing reagents) in methylene chloride and cooling to from −50° to −80° C. and adding dropwise a methylene chloride solution of the avermectin compound to be oxidized. The addition is carried out over a period of from 15 minutes to 1 hour and then triethylamine is added dropwise over a period of from 1 to 15 minutes. The reaction mixture is then allowed to warm to room temperature over a period of from ½ to 1 hour. The 4″-keto compound is isolated using techniques known to those skilled in the art.

The compounds of the instant invention are prepared by reacting the 4″- or 4′- oxo avermectins (compound II) with the appropriately substituted semicarbazides, carbonyl or sulfonyl hydrazides, hydrazines, or hydroxylamines of the formulas:

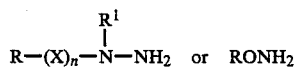

where n, R, R'and X are as defined above. The reaction is carried out in a buffered solution preferably in the presence of pyridine and acetic acid. The solvents may be any non reactive solvent such as methanol, ethanol, isopropanol, and the like. Methanol is preferred. The reaction is generally carried out at room temperatures, 20° to 25° C., but may be heated at temperatures up to 80° C. in order to accelerate the rate. The reaction is usually complete in from 16 to 48 hours at 20° to 25° C. and from 30 to 120 minutes at 80° C. The pH of the reaction greater than 9 or less than 4 are to be avoided since such conditions degrade the avermectin substrate. The products, compound IV which are 4″-or 4′- oxo avermectin semicarbazones, carbonylhydrazones, sulfonylhydrazones hydrazones and oximes, are isolated using techniques known to those skilled in the art. These products are obtained as syn-anti geometric isomers in varying amounts and optionally may be chromatographically separated as shown in Table 4.

These hydrazone products compound IV may be reacted with a reducing agent to reduce the 4″-imino double bond to a single bond compound V. The reaction is carried out with a mild reducing agent such as sodium cyanoborohydride, sodium borohydride, or potassium borohydride and the like, and is carried out in a solvent not susceptable to reduction by the reducing agent, such as methanol, ethanol, isopropanol, and the like. Methanol is preferred. The reaction is carried out at from about 20° to 25° C. and is generally complete in from 1 to 4 hours. 4″-or 4′- deoxyavermectin semicarbazide, carbonyl hydrazide, sulfonylhydrazide, and hydrazine products are obtained and are isolated using techniques known to the art.

PREPARATION OF STARTING MATERIALS

The ultimate starting materials for the compounds of this invention are the avermectin fermentation products defined above, Thus it is apparent that additional reactions are required to prepare the instant compounds. Specifically, reactions are carried out at the 5, 13, 22, and 23-positions and at the 8, 9 and 10, 11 double bonds. It is generally preferred to prepare whatever substituents are required at these positions before the oxidation at the 4″-hydroxy and subsequent substitution on the thus produced 4″-keto. Such a procedure generally avoids undesirable side reactions. This technique is not required, however, and if desired other sequences may be used. In addition, during the oxidation and substitution reaction described above, it is necessary to protect the hydroxy groups at the 5- and 23-positions to avoid oxidation or substitution at such positions. With these positions protected the reactions may be carried out at the 4″-and 4′- positions without affecting the remainder of the molecule. Subsequent to any of the above described reactions the protecting group may be removed and the unprotected product isolated. The protecting group employed is ideally one which may be readily synthesized, will not be affected by the reactions at the 4''- and 4'- positions and may be readily removed without affecting any other functions of the molecule. One preferred type of protecting group for the avermectin type of molecule is the tri substituted silyl group, preferably the trialkyl silyl group. One especially preferred example, is the t-butyl dimethylsilyl group. The reaction preparing the protected compound is carried out by reacting the hydroxy compound with the appropriately substituted silylhalide, preferably the silylchloride in an aprotic polar solvent such as dimethylformamide. Imidazole is added as a catalyst. The reaction is complete in from 1 to 24 hours and at from 0° to 25° C. For the 5-position hydroxy group the reaction is complete in from ½ to 3 hours at from 0° C. to room temperature. This reaction is selective to the 5-position under the conditions above described and very little, if any, silylation is observed at other hydroxy substituted positions. If it is desired to protect the 23-hydroxy group a 4'', 5,23-tri(phenoxyacetyl) derivative can be prepared. Basic hydrolysis will leave the highly hindered 23-O-substituent but hydrolize the 5- and 4''-O-phenoxy acetyl groups. The 5-position is then protected as described above, selectively with a t-butyldimethylsilyl group.

The silyl group is most conveniently removed just prior to hydrazone formation but may be removed as the final step after the other contemplated reactions are carried out. The silyl group or groups are removed by stirring the silyl compound in methanol catalized by an acid preferably a sulfonic acid hydrate such as methanolic 1.0% p-toluene sulfonic acid monohydrate. The reaction is complete in about 1 to 12 hours at from 0° to 50° C. Alternatively the silyl group or groups may be removed by treatment of the silyl compound with anhydrous pyridine hydrogen fluoride in tetrahydrofuran. The reaction is complete in from 3 to 24 hours at from 0° to 25° C.

Another of the starting materials used in the foregoing reaction scheme are those in which the 22,23 double bond of the "1" type compounds has been reduced to a single bond. As is readily apparent from an analysis of the structure of avermectin starting materials there are 5 unsaturations in the l-series of compounds. Thus in the one series of compounds it is necessary to reduce the 22,23 double bond while not affecting the remaining four unsaturations or any other functional group present on the molecule in order to selectively prepare the 22,23 dihydro avermectins. It is necessary to select a specific catalyst for the hydrogenation, one that will selectively hydrogenate the least hindered from among a series of unsaturations. The preferred catalyst for such a selective hydrogenation procedure is one having the formula:

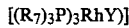

wherein $R_7$ is loweralkyl, phenyl or loweralkyl substituted phenyl and Y is halogen. The reduction procedure is completely described in U.S. Pat. No. 4,199,569.

The other starting materials which are used in the above reaction scheme involve the preparation of the mono saccharide compound. That is those compounds wherein one of the α-l-oleandrosyl groups have been removed. The removal of the terminal a-l-oleandrose leaves a hydroxy group at the 4'-position which is equally amenable to the reactions described in the foregoing reaction scheme. Of course in such a case the products prepared are 4'-keto and 4'-deoxy 4'-amino derivatives rather than the 4''-keto and 4''-deoxy 4''-amino derivatives. The processes which may be used to prepare the monosaccharide derivatives of the avermectin compounds are described in U.S. Pat. No. 4,206,205. The reaction consists generally of treating the starting material disaccharide with acid in an aqueous organic solvent mixture. Water concentrations of from 0.1 to 20% by volume and acid concentrations of from about 0.01 to 0.1% will predominantly produce the monosaccharide product.

A further procedure for the preparation of the monosaccharide utilizes a 1% mineral acid solution in isopropanol at for 20°–40° C. preferably at room temperature for from 6 to 24 hours. Mineral acids such as sulfuric, hydrohalic, phosphoric and the like may be employed.

Some of the compounds of the instant invention differ from other avermectin compounds in that the 10,11 double bond is reduced. The effect of reducing the 10,11 double bond is that the conjugated diene system is broken. The elimination of the conjugated double bonds has a considerable effect on the ultraviolet absorption characteristics of the molecule and has resulted in a surprising and very significant increase in the stability of the molecule when it is exposed to ultraviolet light, as well as ordinary sunlight which has a significant component of ultraviolet light. This increased stability in the presence of ultraviolet light makes these compounds particularly suited to agricultural applications and also to topical animal applications where photoinstability would be detrimental to the optimum performance of each compound.

The 8,9 and 10,11 double bonds of the avermectin starting materials are either reduced catalytically or are chemically modified. The catalytic reduction is carried out using platinum group metals as catalysts such as platinum, palladium, rhodium, and the like. Generally, the metal catalyst is dispersed on and supported on a substrate such as powdered carbon. The reaction is carried out under a blanket of hydrogen gas either at atmospheric pressure or pressurized up to 10 atmospheres (gauge) of hydrogen pressure in pressurable equipment ordinarily used for such reactions. The reaction is carried out in a solvent which is stable to the hydrogenation conditions and which will not adversely affect the catalyst. Lower alkanols, such as methanol, ethanol, isopropanol and the like, ethyl acetate, cyclohexane, and the like are suitable. The reaction is generally carried out at room temperature although temperature as high as 50° C. are suitable and under such conditions the reaction is complete in from 1 to 24 hours. If the hydrogenation apparatus is so equipped, the progress of the reaction may be followed by observing the amount, either in volume or in pressure drop, of hydrogen that is consumed. The products are isolated using techniques known to those skilled in the art.

The catalytic hydrogenation process generally yields a mixture of products since the avermectin starting materials have three or four double bonds which may be hydrogenated. This would include the 3,4 and 22,23 double bonds. The 14,15 double bond is sterically hindered and generally requires more vigorous reaction conditions than are described above in order to effect hydrogenation. The various hydrogenation products are isolated from the mixture of reaction products using standard techniques such as fractional crystallization and chromatography. The double bonds which are desired to be retained in the final product may be protected to render them inert during the hydrogenation procedure. When the hydrogenation is complete, the double bond may be regenerated by removing the protecting groups.

The 10,11 double bond may also be reacted chemically and in the process various substituents at the 10 and 11 positions ($R_5$ and $R_6$ respectively) are introduced according to the following reaction scheme where only the furan ring and carbon atoms 6 to 12 are shown in the partial structural formulas.

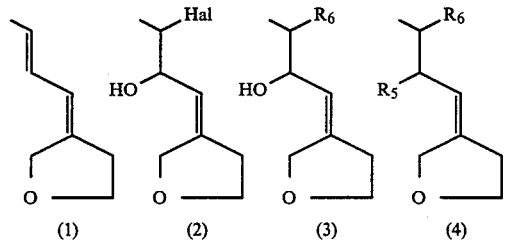

wherein $R_5$, and $R_6$ are as defined above and Hal is a halogen.

Partial structure (1) is reacted with a reagent capable of preparing a halohydrin group (a 10 hydroxy, 11-halo function). Various reagents and reaction conditions are capable of preparing a halohydrin such as N haloacetamide, N-halosuccimide, addition of hydrochloric acid to an epoxide, and the like. Bromine is the preferred halogen. When reagents such as N-haloacetamide and N-halo succinimide are used, the reaction is carried out in an inert solvent, such as acetone, ether, tetrahydrofuran, and the like. The reaction is generally carried out at from $-20°$ to $50°$ C. and is complete in from 30 minutes to 24 hours and is generally carried out in the dark.

The halohydrin compound (2) may be treated with a reducing agent, such as a trialkyltin hydride to displace the halogen with a hydrogen. Partial structures (2) and (3), with the 11-position substituent being a halogen or hydrogen constitutes the definition of $R_5$ as shown in partial structure (3). Further reactions are possible at the 10-position to convert the hydroxy group to the other groups of $R_5$ (partial structure (4)) using techniques known to those skilled in the art.

The epoxide 8,9-compounds of this invention are prepared by treating the appropriately substituted avermectin compound with a mild oxidizing agent. The oxidizing agent should be capable of preparing the epoxide from 8,9 bonds, but not be so strong as to complete cleave the bond or to effect any of the other unsaturations or other functional groups present on the molecule. It has been found that oxidizing agents with such characteristics are exemplified by m chloroperbenzoic acid, alkyl hydroperoxides catalyzed with vanadyl acetylacetonates, and the like.

The reaction is carried out in an inert solvent, not capable of being oxidized, such as methylene chloride, chloroform, and the like. In order to prevent the reaction from becoming too vigorous, it is carried out at moderate temperatures. Generally, room temperature is adequate although cooling to a temperature of about $0°$ C. is acceptable. The reaction is usually complete in a fairly short time, up to about 2 hours, at room temperature. The compounds of this invention are isolated using techniques known to those skilled in the art.

Generally, a slight excess of the oxidizing agent is employed such as from about 10 to 30% excess, when it is desired to prepare the 8,9-epoxide. Larger amounts will tend to affect other reactive groups on the molecule.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as spider ites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excpient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These osage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, lycerol formal, and aqueous parenteral formulations ar also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compounds employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat reinfections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration the parenteral route by injection being preferred for generalized infections. Such matters, however, are left to the routine discretion of the therapist according to principles of treatment well known in the antibiotic art. In general, a daily dosage consists of from about 0.1 to about 5 mg of active ingredient per kg. of body weight of the subject in one or more treatments per day. A preferred daily dosage for mature animals lies in the range of from about 0.1 to 20 mg. of active ingredient per kg. of body weight. Another factor influencing the precise dosage regimen, apart from the nature of the infection and peculiar identity of the individual being treated, is the molecular weight of the chosen species of this invention.

The compositions for delivery per unit dosage, whether liquid or solid, may contain from 0.1% to 99% of active material, the preferred range being from about 10-60%. The composition will generally contain from about 5 mg. to about 50 mg. of the active ingredient; however, in general, it is preferable to employ a dosage amount in the range of from about 5 mg to 100 mg. In parenteral administration, the unit dosage is usually the pure compound I in sterile solution or in the form of a soluble powder intended for solution.

In the isolation of the avermectin compounds, which serve as starting materials for the instant process, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular it has been found that the starting materials for the compounds of this invention are very often prepared in a ration of about 80% avermectin B1a or A1a and 20% avermectin B1b or A1b. Thus the preferred composition of this invention is one which contains more than about 80% of the "a" component and less than about 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

In the following examples, the various starting materials therefor are avermectin compounds or derivatives of avermectin compounds. The avermectin compounds and the preparation and isolation thereof from fermentation broths are described in U.S. Pat. No. 4,310,519 issued 12 January 1982. The 4"- and 4'- keto starting materials are described in U.S. Pat. No. 4,427,663, and, the 8,9 epoxide compounds are described in U.S. Pat. No. 4,530,921. The selective 22,23-dihydro derivatives of avermectin compounds are described in U.S. Pat. No. 4,199,569 issued 22 April 1980. The monosaccharide derivatives of avermectin compounds are described in U.S. Pat. No. 4,206,205 issued 3 January 1980.

EXAMPLE 1

5-O-t-butyl-dimethylsilyl 22,23-dihydro avermectin B1a/B1b 3 g of 22,23-dihydro avermectin B1a/B1b in 30 ml of dry dimethylformamide was combined with 1.4 g of imidazole and stirred at room temperature until all the materials had dissolved. Then 1.56 g of t-butyl dimethylsilyl chloride was added and the reaction mixture stirred at room temperature for 70 minutes. The reaction mixture was diluted with 150 ml of ether, water was added and the layers were separated. The aqueous layer was extracted twice more with ether and the combined ether layers washed four times with water and once with saturated sodium chloride solution. The ether layer was dried over magnesium sulfate and concentrated to dryness in vacuo affording 4.2 g of a white foam. The foam is chromatographed on 135 g. of 70-230 mesh silica gel and eluted with 5% tetrahydrofuran in methylene chloride. 1.15 G of 4",5-di-O-t butyl-dimethylsilyl-22,23-dihydro avermectin B1a/B1b and 2.6 g of 5-O-t-butyl dimethylsilyl 22,23 dihydro avermectin B1a/B1b were recovered as pure amorphous foams.

EXAMPLE 2

5-O-t-butyl-dimethylsilyl-4"-oxo-22,23-dihydro avermectin B1a/B1b

In a dried flask purged with dry nitrogen was placed 97 μl of oxalyl chloride and 1.5 ml of methylene chloride. The reaction mixture was cooled to 60° C., 1 ml of the methylene chloride solution containing 160 μl of dimethylsulfoxide was added over a period of 3 minutes and the reaction mixture stirred at −60° C. for two minutes. 3 Ml of methylene chloride containing 500 mg of 5-O-t-butyl-dimethylsilyl 22,23-dihydro avermectin B1a/B1b was added dropwise over a period of 5 minutes and the reaction mixture stirred at room temperature for 30 minutes. At the end of this period, 0.71 ml of triethylamine was added dropwise and the reaction mixture was stirred at 60° C. for 5 minutes. The cold bath was removed and the reaction mixture was allowed to come to room temperature over a period of 45 minutes. 50 Ml of water was added and the reaction mixture was extracted 3 times with 40 ml of ether. The ether extracts were combined and washed 4 times with 20 ml of water, dried over magnesium sulfate and concentrated to dryness in vacuo affording 520 mg of a yellow glass. The yellow glass was dissolved in methylene chloride and placed on three 2.0 mm thick silica gel preparative layer chromatography plates. The plates were developed with 10% ethyl acetate in methylene-chloride and afforded 470 mg of yellow foam which was characterized by its 300 MHz nuclear magnetic resonance spectrum as 5-O-t-butyl-dimethyl silyl-4"-oxo-22,23-dihydro avermectin B1a/B1b.

EXAMPLE 3

5-O-tert-Butyldiphenylsilyl-10,11,22,23-tetrahydro avermectin B1a/B1b

A solution of 1.1 g 5-O-tert-butyldiphenylsilyl avermectin B1a/B1b in 10 ml of absolute ethanol and 0.2 g of 5% palladium on carbon was shaken in a Parr hydrogenator with hydrogen at 90 pounds pressure at room temperature until the drop in pressure indicated the uptake of one molar equivalent. The hydrogenation was stopped and a small sample was withdrawn for analysis. High performance liquid chromatographic analysis on a reverse phase $C_{18}$ column with a methanol-water liquid phase indicated the major components to be the 5-O-tert-butyldiphenylsilyl-22,23-dihydroavermectin B1a/B1b. The Parr hydrogenator was charged with another 0.2 g 5% Pd/C and the system repressurized to 84 lbs with hydrogen. After another pressure drop indicated the uptake of another molar equivalent of hydrogen, the catalyst was removed by filtration. Evaporation of the filtrate afforded a mixture of which the title compound is a major component. HPLC purification with a preparative reverse phase $C_{18}$ column using a methanol water liquid phase affords 5-O-tert-butyldiphenylsilyl-10,11,22,23-tetrahydro avermectin B1a/B1b as an amorphous solid characterized by its $^1$H NMR and mass spectrum.

EXAMPLE 4

10,11,22,23-Tetrahydroavermectin B1a/B1b

A solution of 25 mg of 5-O-tert-butyldiphenylsilylavermectin B1a/B1b in 1 ml of tetrahydrofuran was desilylated using 3 ml of an anhydrous hydrogen fluoride pyridine in THF solution which was prepared from 14 mL of THF, 4 ml of pyridine, and 2 ml of a commercial hydrogen fluoride pyridine solution (consisting of ~70% HF and ~30% pyridine, supplied by Aldrich Chemical Company) at room temperature for 20 hours under nitrogen. The reaction was worked up by addition of water followed by neutralization with sodium bicarbonate solution and extraction with ether. The ether extracts were combined and evaporated to yield a residue which was charged onto two 500 micron preparative silica gel plates. Elution with a hexane ethyl acetate solvent afforded 10,11,22,23-tetrahydroavermectin B1a/B1b as an amorphous solid which was characterized by its $^1$H NMR and mass spectrum (molecular ion 876).

EXAMPLE 5

10,11,22,23-Tetrahydroavermectin B1a/B1b and 3,4,10,11,22,23 Hexahydroavermectin B1a/B1b A solution of 10.0 g of 22,23 dihydroavermectin $B_1$ (containing approximately 90% of 22,23-dihydroavermectin B1a and 9% of the lower homolog B1b) in 100 ml of absolute ethanol was shaken in the presence of 2.5 g of 5% palladium on charcoal catalyst under an atmosphere of hydrogen at 89 pounds of pressure at room temperature for one hour, when the drop in hydrogen pressure indicated the uptake of one molar equivalent. The hydrogenation was stopped, the catalyst removed by filtration, and the filtrate was concentrated to give 9.9 g of a white foam. High performance liquid chromatography on a reverse phase $C_{18}$ column with a $CH_3CN$—MeOH—$H_2O$ liquid phase suggested a composition of the crude reaction product of 23% 22,23-dihydroavermectin B1a/B1b, 46% 10,11,22,23-tetrahydroavermectin B1a/B1b and several other unidentified compounds. 8.7 Grams of the crude product were further purified on a silica gel column with a hexane-acetone system as solvent to give 3.8 g enriched in the desired 10,11,22,23 tetrahydroavermectin B1. The final purification was achieved with an aliquot of 500 mg via preparative reverse phase high performance liquid chromatography with a MeOH—$H_2O$ liquid phase which gave 280 mg of 10,11,22,23-tetrahydroavermectin B1a as a white amorphous solid after lyophilization from a benzene solution. It was characterized by its $^1$H NMR and its mass spectrum, which has a molecular ion for the mass of 876, and its UV spectrum which lacks the absorption at 245 nm. Further fractionations as described above yield 10,11,22,23-tetrahydroavermectin B1b, 3,4,10,11,22,23-hexahydroavermectins B1a and B1b. The mass spectrum for 10,11,22,23-tetrahydroavermectin B1a revealed major peaks at 876 (M+) and 588 (tetrahydroaglycone). The nuclear magnetic resonance spectrum of the compound (400 MHz in CDCl$_3$ with TMS as an internal standard) revealed the following major peaks: 4.3 ppm (t, 1H, J=6 Hz) for C5 H; 4.55 ppm (tq, 2H, J=2, 17 Hz) for 8a-H2; 4.73 ppm (d, 1H, J=3 Hz) for 1'-H; 5.01 ppm (brd, 1H, J=10 Hz) for $C_{15}$-H; 5.14 ppm (S, $^1$H) for 7 OH; 5.32 ppm (dd, 1H) for $C_9$-H; 5.34 ppm (S, 1H) for $C_3$-H; 5.4 ppm (m, 1H) for $C_{19}$ H; 5.4 ppm (d, 1H, J=3 Hz) for

EXAMPLE 6

10,11-Dihydroavermectin B2a/B2b and 3,4,10,11 tetradroavermectin B2a/B2b

A solution of 870 mg avermectin B2a/B2b in 25 ml of absolute ethanol and 100 mg of 5% Pd/C was stirred at room temperature under one atmosphere pressure of hydrogen. After an uptake of 1.5 molar equivalent of hydrogen, the catalyst was removed by filtration. HPLC analysis using a reverse phase $C_{18}$ column and a methanol-water liquid system indicated the composition of the mixture to be 18% avermectin B2a/B2b, 45% 10,11-dihydroavermectin B2a/B2b, 27% 3,4-dihydroavermectin B2a/B2b, and 9% 3,4,10,11-tetrahydroavermectin B2a/B2b. Preparative HPLC using a reverse phase $C_{18}$ column and a methanol-water system followed the separation and characterization of each of the titled compounds via their 1H NMR and mass spectra.

EXAMPLE 7

5-O-tert Butyldimethylsilyl avermectin B1a/1b

Avermectin B1a/1b, 27.6 g (31.7 mmole), was reacted with imidazole, 15.3 g (225 mmole), and t-butyldimethylsilyl chloride, 12.8 g (84.9 mMole), in 130 ml of dry dimsthylformamide following the procedure of Example 1 furnishing 38 g of solids which were chromatographed on a column of silica gel using methylene chloride ethyl acetate (92.5:7.5 85:15). 5-O-tert-Butyldimethylsilyl avermectin B1a/B1' b 24.7 g, was obtained and characterized by nuclear magnetic resonance, mass spectra [987 $(M+H)^+$] and high pressure liquid chromatographic analyses.

EXAMPLE 8

5-O-tert-Butyldimethylsilyl-4''-oxoavermectin B1a/B1b

5-O-tert-Butyldimethylsilyl avermectin B1a/B1b, 20.0 (20.3 mMole), was reacted with oxalyl chloride, 4.0 ml (46 mMole), dimethylsufoxide, 6.3 ml (89 mMole), and triethylamine, 27.8 ml (200 mMole) in 220 ml of dry methylene chloride following the procedure of Example 2 furnishing 5-O-tert-butyldimethylsilyl-4''-oxoavermectin B1a/B1b, 17.2 g, which was used without chromatographic purification. This product was characterized by nuclear magnetic resonance, mass spectra [985 $(M+H)^+$] and high pressure liquid chromatographic analyses.

EXAMPLE 9

4''-Oxoavermectin B1a/B1b

A cold (0° to 5° C.) solution of 5-O-tert-butyldimethylsilyl-4'-oxoavermectin B1a/B1b, 5.50 g (5.40 mMole), and methanolic 1.0% p-toluenesulfonic acid monohydrate, 120 ml (6.2 mMole), was stirred for 50 minutes and then poured into aqueous sodium bicarbonate. The product was extracted with methylene chloride. The methylene chloride solutions were combined, dried over anhydrous sodium sulfate and evaporated under reduced pressure providing 4.5 g of 4''-oxoavermectin B1a/B1b which were characterized by nuclear magnetic resonance, mass spectra [871 $(M+H)^+$] and high pressure liquid chromatographic analyses.

EXAMPLE 10

2-(4-Nitrophenoxycarbonylamino)thiazole

A solution of 4-nitrophenyl chloroformate, 5.04 g (25 mMole), in 25 ml of dry ethyl acetate was added dropwise to an ice cooled, stirred solution of 2-aminothiazole, 5.01 g (50 mMole) in dry ethyl acetate, 25 ml, and dry pyridine, 50 ml. The ice bath was removed as the reaction mixture became viscous. Stirring was continued at 22° C. for three hours. Ethyl acetate was added. The insolubles were filtered, rinsed with ethyl acetate, with water, with acetone, dried and recrystallized from acetone furnishing 3.55 g of 2-(4-nitrophenoxycarbonyl)aminothiazole, m.p 211°–212° C. dec, which was characterized by nuclear magnetic resonance, mass spectra, infrared spectra and elemental analyses.

EXAMPLE 11

1-(4-Nitrophenoxycarbonyl)-4-methylpiperazine

A solution of 4-nitrophenyl chloroformate, 5.04 g (25 mMole) in 25 ml of dry ethyl acetate was added dropwise to an ice bath cooled, stirred solution of N-methylpiperazine, 5.55 ml (50 mMole), and N,N-diisopropylethylamine, 5.23 ml (30 mMole), in 50 ml of dry ethyl acetate. The ice bath was removed and stirring was continued at 22° C. for three hours. The thick reaction mixture was diluted with ethyl acetate, extracted with aqueous sodium bicarbonate and saturated aqueous sodium chloride, dried over sodium sulfate and evaporated under reduced pressure. The solid residue was recrystallized from methylene chloride hexane furnishing 3.67 g of 1-(4-nitro-phenoxycarbonyl)-4-methylpiperazine, m.p. 134°–135° C., which was characterized by nuclear magnetic resonance, mass spectra, infrared spectra and elemental analyses.

TABLE 1

N—Nitrophenylcarbamate Intermediates Prepared Following the Procedure of Example 11

$$O_2N-\text{C}_6H_4-OC(O)-Cl + RRNH \longrightarrow O_2N-\text{C}_6H_4-OCNRR$$

| RRNH | Product | M.P. (°C.) | Analyses |
|---|---|---|---|
| 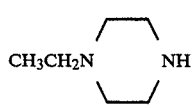 CH$_3$CH$_2$N⌒NH | 2-(4-Nitrophenoxycarbonyl-amino)-4-ethylpiperazine | 90–91 | A, B, C, D |

TABLE 1-continued

N—Nitrophenylcarbamate Intermediates Prepared Following the Procedure of Example 11

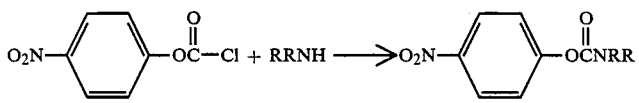

| RRNH | Product | M.P. (°C.) | Analyses |
|---|---|---|---|
| (CH$_3$)$_2$CHNHCCH$_2$N⟨ ⟩NH (with C=O) | 1-(4-Nitrophenoxycarbonyl)-4-(isopropylaminocarbonyl methyl)piperazine | 127–129 | A, B, C, D |
| (CH$_3$)$_2$NCH$_2$CH$_2$NH$_2$ | N—Dimethyl-N'—(4-nitrophenoxy-carbonyl)ethylenediamine | | |
| CH$_3$OCH$_2$CH$_2$NH$_2$ | 2-methoxy-N—(4-nitrophenoxy-carbonyl)ethylamine | 75 | A, B, C, D |

A Proton nuclear magnetic resonance analysis.
B Mass spectral analysis.
C Infrared spectral analysis.
D Elemental analysis.

EXAMPLE 12

4-(Thiazol-2-yl)semicarbazide

A solution of 2-(4-nitrophenoxycarbonyl)aminothiazole, 3.5 g (13 mMole) and 85% hydrazine hydrate, 4.0 ml (69 mMole) in 40 ml of methanol was stirred under nitrogen at 22° C. for 10 days. The mixture was cooled in ice. The insolubles were filtered, washed with cold methanol, dried and recrystallized from ethanol furnishing 780 mg of (thiazol-2-yl)semicarbazide, m.p. 166°–167° C., which was characterized by nuclear magnetic resonance, mass spectra, infrared spectra and elemental analyses.

EXAMPLE 13

4-(Benzothiazol-2-yl)semicarbazide

A solution of 4-nitrophenyl chloroformate, 5.04 g (25 mMole) in 25 ml of dry chloroform was added dropwise to a to a ice cooled, stirred solution of 2-aminobenzothiazole, 3.75 gm (25 mMole) in 50 ml of dry pyridine. The mixture was stirred at 0° C. for 45 minutes longer. Anhydrous hydrazine, 1.6 ml (250 mMole), was added rapidly to the stirred reaction mixture and the ice bath was removed. Stirring was continued for 3 hours at 22° C. Insolubles were filtered, rinsed with cold methanol and dissolved in dilute aqueous hydrochloric acid. Insolubles were filtered off and the aqueous solution was extracted with ethyl acetate. The aqueous solution was made basic, pH 9.5, by addition of aqueous sodium hydroxide. The insoluble product was filtered, washed with water, dried, and recrystallized from ethanol furnishing 1.35 g of 4-(benzothiazol-2-yl)-semicarbazide melting at 225° C. The product was characterized by nuclear magnetic resonance, mass spectra, infrared spectra and elemental analyses.

TABLE II

Semicarbazide Intermediates Prepared Following the Procedure of Example 13

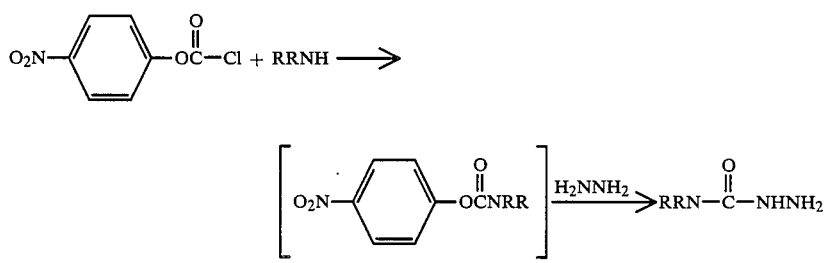

| RRNH | Product | M.P. (°C.) | Analyses |
|---|---|---|---|
| pyrimidin-2-yl-NH$_2$ | 4-(pyrimidin-2-yl)semicarbazide | 249–250 | A, B, C, D |
| Cl—C$_6$H$_4$—N⟨ ⟩N—H (piperazine) | 4-(4-Chlorophenyl)piperazine-1-carboxylic acid hydrazide | 154–155 | A, B, C, D |

TABLE II-continued
Semicarbazide Intermediates Prepared Following the Procedure of Example 13

$$O_2N-C_6H_4-OC(O)-Cl + RRNH \longrightarrow [O_2N-C_6H_4-OCNRR] \xrightarrow{H_2NNH_2} RRN-C(O)-NHNH_2$$

| RRNH | Product | M.P. (°C.) | Analyses |
|---|---|---|---|
| CH$_3$-C$_6$H$_4$-N(piperazine)NH | 4-(4-Toyly)piperazine-1-carboxylic acid hydrazide | 158–160 | A, B, C, D |
| CH$_3$O-C$_6$H$_4$-N(piperazine)NH | 4-(4-Methoxyphenyl)peiperazine-1-carboxylic acid hydrazide | 153 | A, B, C, D |
| H$_2$NSO$_2$-C$_6$H$_4$-NH$_2$ | 4-(4-Sulfamylphenyl) semicarbazide | 230–235 | A, B, C, D |

A, B, C and D see footnotes for Table I

EXAMPLE 14
4-Methylpiperazine-1-carboxylic acid hydrazide dihydrochloride A solution of 1-(4-nitrophenoxycarbonyl)-4-methylpiperazine, 3.5 g (13 mMole) and 85% hydrazine hydrate, 4.0 ml (69 mMole) in 40 ml of methanol was stirred under nitrogen at 22° C. for three days. The reaction solution was evaporated under reduced pressure The solid residue was dissolved in dilute hydrochloric acid and extracted with ethyl acetate. The aqueous solution was made basic, pH 9.5, with aqueous sodium hydroxide and evaporated under reduced pressure leaving a solid. The residue was triturated with methylene chloride which was evaporated. The methylene chloride extractives were dissolved in 50 ml of methanol and cooled in ice. 2.1 ml of concentrated hydrochloric acid was added with stirring followed by 200 ml of ethyl ether. The product separated and was collected furnishing 2.24 g of 4-methylpiperazine 1-carboxylic acid hydrazide dihydrochloride, m.p. 191°–192° C., which was characterized by nuclear magnetic resonance, mass spectra, infrared spectra and elemental analyses.

TABLE III
Semicarbazide Intermediates Prepared Following the Procedure of Example 14

$$O_2N-C_6H_4-OCNRR + H_2NNH_2 \longrightarrow RRNCNHNH_2$$

| RRN | Product | M.P. (°C.) | Analyses[1] |
|---|---|---|---|
| CH$_3$CH$_2$-N(piperazine)N- | 4-Ethylpiperazine-1-carboxylic acid hydrazide dihydrochloride | 202–203 | A, B, C, D |
| (CH$_3$)$_2$CHNHCCH$_2$N(piperazine)N- | 4-(Isopropylaminocarbonylmethyl)piperazine-1-carboxylic acid hydrazide dihydrochloride | 200–201 | A, B, C, D |
| (CH$_3$)$_2$NCH$_2$CH$_2$N- | 4-(Dimethylaminoethyl) semicarbazide dihydrochloride | | |
| CH$_3$OCH$_2$CH$_2$N- | 4-(2-methoxyethyl) | 120–121 | A, B, C, D |

TABLE III-continued
Semicarbazide Intermediates Prepared Following the Procedure of Example 14

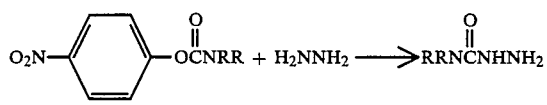

| RRN | Product | M.P. (°C.) | Analyses[1] |
|---|---|---|---|
| | semicarbzide hydrochloride[2] | | |

[1] A, B, C and D see footnotes for Table I
[2] Free base purified by silica gel chromatography

EXAMPLE 15

4-(1H-Benzimidazol-2-yl)semicarbazide

A solution of methyl 1H-benzimidazole-2-yl carbamate, 1.0 g, and anhydrous hydrazine, 4.0 ml, in 40 ml of dry pyridine was stirred at 22° C. under nitrogen for 24 hours and then at 60° C. for 18 hours. The solution was evaporated to dryness under reduced pressure and the residue was crystalized from isopropanol furnishing 310 mg of 4-(1H-benzimidazol-2-yl) semicarbazide, m.p. 320°–322° C., which was characterized by nuclear magnetic resonance and mass spectra analyses.

EXAMPLE 16

4"-Oxoavermectin B1a/B1b 4-(1H-benzimidazol-2-yl) semicarbazone, Isomers A and B A solution of 4"-oxoavermectin B1a/B1b, 300 mg (345 μMole), 4-(1H-benzimidazol-2-yl)semicarbazide, 99 mg (518 μMole) and glacial acetic acid, 30 μl (518 Mole) in 2 ml of dry methanol and 3.0 ml of dry hyridine was stirred at room temperature, 23° C., for 42 hours. The reaction mixture was diluted with isopropanol and evaporated under reduced pressure. The residue was taken up in methylene chloride. The solution was extracted with aqueous sodium bicarbonate, dried over sodium sulfate and evaporated under reduced pressure leaving 580 mg of solids. The solids were chromatographed on silica gel using methylene chloride ethyl acetate isopropanol (80:20:0.5 to 3) furnishing 131 mg of isomer A of the 4"-oxoavermectin B1a/B1b 4-(1H-benzimidazole-2-yl)semicarbazone, and 73 mg of the isomer B which were characterized by nuclear magnetic resonance, mass spectra B, and [1044(M+H)+], and high pressure liquid chromatographic analyses.

TABLE IV
4"-Oxoavermecting B1a/B1b 4-Substituted Semicarbazones Prepared Following the Procedure of Example 16

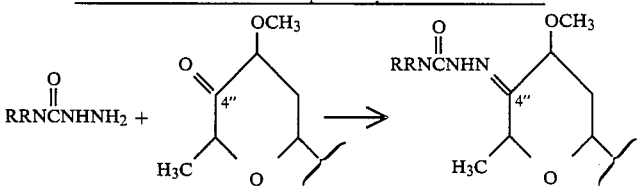

| RRN—Substituent | 4"-Oxoavermectin B1a/1b Product | Isomers[1] | (M + M)+ | Analyses[2] |
|---|---|---|---|---|
| CH₃NH— | 4-methylsemicarbazone | A + B | 942 | A, B, C |
| (CH₃)₂N— | 4,4-dimethylsemicarbazone | A + B | 956 | A, B, C |
| morpholin-4-yl— | 2-[(morpholin-4-yl)carbonyl]hydrazone | A + B | 998 | A, B, C |
| thiazol-2-yl—NH— | 4-(thiazol-2-yl) semicarbazone | A / B | 1011 / 1011 | A, B, C / A, B, C |
| benzothiazol-2-yl—NH— | 4-benzothiazol-2-yl) semicarbazone | A / B | 1061 / 1061 | A, B, C / A, B, C |
| pyrimidin-2-yl—NH— | 4-(pyrimidin-2-yl) semicarbazone | A + B | 1006 | A, B, C |

TABLE IV-continued

4"-Oxoavermecting B1a/B1b 4-Substituted
Semicarbazones Prepared Following the Procedure of
Example 16

| RRN—Substituent | 4"-Oxoavermectin B1a/1b Product | Isomers[1] | (M + M)+ | Analyses[2] |
|---|---|---|---|---|
| Cl—⬡—NH— | 4-(4-chlorophenyl) semicarbazone | A + B | 1038 | A, B, C |
| CH$_3$—N⬡N— | 2-[(4-methylpiperazin-1-yl) carbonyl]hydrazone | A<br>B | 1011<br>1011 | A, B, C<br>A, B, C |
| CH$_3$CH$_2$N⬡N— | 2-[(4-ethylpiperazin-1-yl) carbonyl]hydrazone | A + B | 1025 | A, B, C |
| (CH$_3$)$_2$CHNCCH$_2$N⬡N— | 2-{[4-(isopropylaminocarbonyl-methyl)piperazin-1-yl] carbonyl}hydrazone | A + B | 1096 | A, B, C |
| Cl—⬡—N⬡N— | 2-{[4-(4-chlorophenyl) piperazin-1-yl] carbonyl}hydrazone | A + B | 1107 | A, B, C |
| CH$_3$—⬡—N⬡N— | 2-{[(4-tolyl)piperazin-1-yl] carbonyl}hydrazone | A + B | 1087 | A, B, C |
| CH$_3$O—⬡—N⬡N— | 2-{[4-(4-methoxyphenyl) piperazin-1-yl] carbonyl}hydrazone | A + B | 1103 | A, B, C |
| H$_2$NSO$_2$—⬡—NH— | 4-(4-sulfamylphenyl) | A + B | 1082 | A, B, C |
| (CH$_3$)$_2$NCH$_2$CH$_2$NH— | 4-(dimethylaminoethyl) semicarbazone | A + B | — | — |
| CH$_3$O CH$_2$ CH$_2$ NH— | 4-(methoxyethyl) semicarbazone | A + B | 986 | A, B, C |

[1]Syn/Anti geometric isomers
[2]A Proton nuclear magnetic resonance.
B Mass spectra.
C High pressure liquid chromatography.

EXAMPLE 17

4"Oxoavermectin B1a/B1b acethydrazone

A solution of 4"-oxoavermectin B1a/B1b, 200 mg, acethydrazide, 34 mg, glacial acetic acid, 24 µl, and pyridine, 100 µl in 1.2 ml of methanol was stirred at room temperature, 23° C., for 19 hours and then evaporated under reduced pressure. The residue was taken up in methylene chloride, extracted with aqueous sodium bicarbonate, dried over sodium sulfate and evaporated under reduced pressure. The residue was chromatographed on a column of silica gel using 1.0 to 3.0% methanol in methylene chloride furnishing 101 mg of 4"-oxoavermectin B1a/B1b acethydrazone which was characterized by nuclear magnetic resonance, mass spectra [927 (M+H)+] and high pressure liquid chromatographic analyses.

TABLE V

4″-Oxoavermectin B1a/1b Carbonyl- and Sulfonyl Hydrazones Prepared Following the Procedure of Example 17

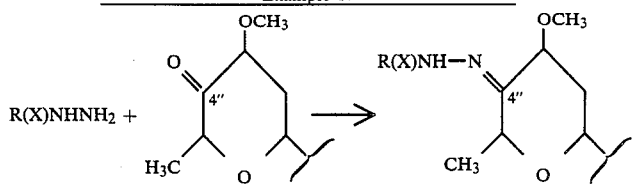

(X = $SO_2$ or CO)

| R(X)NHNH₂ | | Reaction Time | Temp | 4″-Oxoavermectin B1a/B1b Product | (M + H)⁺ | Analyses[1] |
|---|---|---|---|---|---|---|
| $CH_3$— | O<br>‖<br>—CNHNH₂ | 4 days | 23° C. | 4-toluic acid hydrazone | 1003 | A, B, C |
| Cl— | O<br>‖<br>—CNHNH₂ | 8 days | 60° C. | 4-chlorobenzoic acid hydrazone | 10035 | A, B, C |
| $CH_3SO_2NHNH_2$ | | 2 days | 23° C. | methylsulfonyl hydrazone | 963 | A, B, C |
| $CH_3$— | —$SO_2NHNH_2$ | 2 days | 23° C. | 4-toluenesulfonyl hydrazone | 1039 | A, B, C |
| $H_2NSO_2$— | O<br>‖<br>—CNHNH₂ | | | 4-Sulfamylbenzoic acid hydrazone | | |

[1]See footnotes for Table IV

EXAMPLE 18

4″- and 4″-(semicarbazide-1-yl)-4″-deoxy-5-O-tert-butyldimethylsilylavermectins B1a/B1b A solution of 5-O-tert-butyldimethylsilyl-4″-oxoavermectin B1a/B1b, 797 mg (0.80 mMole), semicarbazide hydrochloride, 892 mg (8.0 mMole) and diisopropylethylamine, 230 μl (4.0 mMole) in 6.4 ml of methanol was stirred at room temperature, 23° C., for two hours. A solution of sodium cyanoborohydride, 107 mg (1.7 mMole) in 1.0 ml of methanol was added dropwise over 30 minutes. The mixture was stirred for four hours longer and then diluted with aqueous sodium bicarbonate and methylene chloride. The aqueous layer was separated and extracted with methylene chloride. The methylene chloride solutions were combined, dried over sodium sulfate and evaporated under reduced pressure. The residue was chromatographed on a column of silica gel using 0.5 to 2.0% methanol in methylene chloride furnishing a mixture of the 4″-and 4″-epi-(semicarbazide 1-yl)-4″-deoxy-5-O-tert-butyldimethylsilylavermectins B1a/B1b, 259 mg, which was characterized by nuclear magnetic resonance, mass spectra 44 (M+H)⁺] and high pressure liquid chromatographic analyses.

EXAMPLE 19

4″-(Semicarbazide-1-yl)-4″-deoxyavermectin B1a/B1b and 4″-epi (semicarbazide-1-yl)-4″-deoxyavermectin B1a/B1b A solution of 5-O-tert butyldimethylsilyl-4″-oxoavermectin B1a/B1b 4″- and 4″-epi-semicarbazides, 250 mg (239 Mole) and mathanolic 1.0% p-toluenesulfonic acid monohydrate, 9.1 ml (479 μMole), in 13.4 ml of methanol was stirred at −12° C. for 20 hours. Aqueous sodium bicarbonate was added and the mixture was extracted with methylene chloride. The methylene chloride solutions were combined, extracted with aqueous sodium bicarbonate, dried over sodium sulfate and evaporated under reduced pressure. The residue was chromatographed on a column of silica gel using methylene chloride-ethanol (99:1) furnishing 21 mg of 4″-(semicarbazide1-yl)-4″-deoxyavermectin B1a/B1b and 108 mg of 4″-epi-(semicarbazide-1-yl)-4″-deoxyavermectin B1a/B1b which were characterized by nuclear magnetic resonance, mass spectra [930 (M+H)⁺] and high pressure liquid chromatographic analyses.

EXAMPLE 20

4″-epi-(4-Methylsemicarbazid-1-yl)-4″-deoxyavermectin B1a/B1b

4″-Oxoavermectin B1a/B1b, 600 mg was reacted with 4-methylsemicarbazide and sodium cyanoborohydride and the product was purified as described for Example 18 furnishing 195 mg of 4″-epi-(4-methylsemicarbazid- 1-yl)-4″-deoxyavermectin B1a/B1b, which was characterized by nuclear magnetic resonance, mass spectra [944 (M+H)⁺] and high pressure liquid chromatographic analyses.

EXAMPLE 21

4″-[2-p-Toluic acid)hydrazid-1-yl]-4″-deoxyavermectin B1a/B1b

4″-Oxoavermectin B1a/B1b, (600 mg) was reacted with p-toluic acid hydrazide and sodium cyanoborohydride as described in Example 18. After the initial chromatography, the product was rechromatoraphed on a column of silica using hexane-ethyl acetate-isopropanol (50:50:2) furnishing 105 mg of 4″[2-(p-toluic acid)hydrazid-1-yl]-4″-deoxyavermectin B1a/B1b, which was characterized by nuclear magnetic resonance, mass spectra [1005 (M+H)⁺] and high pressure liquid chromatographic analyses.

EXAMPLE 22

4"-[2-(Toluenesulfonyl)hydrazid-1-yl]-4"-deoxyavermectin B1a/B1b

4"-Oxoavermectin B1a/B1b, (600 mg) was reacted with p-toluenesulfonylhydrazide and sodium cyanoborohydride as described in Example 18. After the initial chromatography, the product was rechromatographed again on a column of silica gel using ethyl ether-petroleum ether (50:50) furnishing 126 mg of 4"-[2-(toluenesulfonyl) hydrazid-1-yl-4"-deoxyavermectin B1a/B1b, which were characterized by nuclear magnetic resonance, mass spectra [1041 (M+H)+] and high pressure liquid chromatographic analyses.

EXAMPLE 23

4"-epi-(2,2,-Dimethylhydrazin-1-yl)-4"'-deoxyavermectin B1a/B1b hydrazine and sodium cyanoborohydride and the product was purified as described in Example 18 furnishing 319 mg of
4"-epi-(2,2-dimethylhydrazin-1-yl)-4"-deoxy-5-O-tert-butyldimethylsilyl-avermectin B1a/B1b, which was characterized by nuclear magnetic resonance, mass spectra [1029 (M+H)+] and high pressure liquid chromatographic analyses.

EXAMPLE 24

4"-epi-(2,2-Dimethylhydrazin-1-yl)-4"'-deoxyavermectin B1a/B1b

4"-epi-(2,2-Dimethylhydrazin-1-yl) 4"deoxy-5-O-tert butyldimethylsilylavermectin B1a/B1b, 319 mg, and 1.0% p-toluenesulfonic acid monohydrate were reacted and the product was purified as described in Example 19 furnishing 128 mg of 4"-epi-(2,2-dimethylhydrazin-1-yl) 4"'-deoxyavermectin B1a/B1b, which was characterized by nuclear magnetic resonance, mass spectra [915 (M+H)+] and high pressure liquid chromatographic analyses.

EXAMPLE 25

4"'-epi (Morpholin-4-yl)amino-4"-deoxy-5-O-tert-butyldimethylsilylavermectin B1a/B1b 5-O-tert-Butyldimethylsilyl-4"-oxoavermectin B1a/B1b, 787 mg, was reacted with 4-aminomorpholine and sodium cyanoborohydride and the product was purified as described in Example 18 furnishing 138 mg of 4"epi-(morpholin-4-yl)amino-4"-deoxy 5-O-tert-butyldimethylsilylavermectin B1a/B1b, which was characterized by nuclear magnetic resonance, mass spectra [1071 (M+H)+] and high pressure liquid chromatographic analyses.

EXAMPLE 26

4"-epi-(Morpholin-4-yl)amino-4"-deoxyavermectin B1a/B1b

4"-epi-(Morpholin-4-yl)amino 4"deoxy-5-O-tert-butyldimethylsilylavermectin B1a/B1a, 188 mg, and 1.0% p-toluenesulfonic acid monohydrate were reacted and the product was purified as described in Example 19 furnishing 145 mg of 4"-epi-(morpholin-4-yl)amino-4"'-deoxyavermectin B1a/B1b, which was characterized by nuclear magnetic resonance, mass spectra [957 (M+H)+] and high pressure liquid chromatographic analyses.

EXAMPLE 27

22,23-Dihydro-4"-oxo 5-O-tert butyldimethylsilyl-avermectin B1a/B1b

To a solution of 97 μl of oxalyl chloride in 2.5 ml of $CH_2Cl_2$ stirred at $-60°$ C. a solution of 160 μl of dimethylsulfoxide in 1.0 ml of $CH_2Cl_{12}$ was added dropwise over 3 minutes from a syringe. Then a solution of 500 mg of 22,23-dihydro 5-O-tert-butyldimethylsilyl-avermectin B1a/B1b in 3.0 ml of $CH_2Cl_2$ was added by syringe dropwise during 5 minutes. The reaction mixture was stirred at $-60°$ C. for 30 minutes, when 0.71 ml of triethylamine was added dropwise. After another 5 minutes at $-60°$ C. the cooling bath was removed, and the reaction mixture was allowed to come to room temperature. Addition to water, extraction with ether, washing with water, drying and concentration in vacuo gave 520 mg of a yellow foam, which was purified by preparative layer silica gel chromatography with a $CH_2Cl_2$-EtOAc-9:1 solvent mixture to give 470 mg of pure 22,23-dihydro-4"-oxo 5-O-tert-butyldimethylsilylavermectin B1a/B1b, which was characterized by its mass and 300 mHz $^1$H-NMR spectra.

EXAMPLE 28

22,23-Dihydro-4"-oxo-5-O-tert-butyldimethylsilylavermectin B1a/B1b semicarbazone A solution of 3.0 ml of MeOH containing 22,23-dihydro-4"-oxo-5-O-tert butyldimethylsilylavermectin B1a/B1b (50 mg), semicarbazide hydrochloride (14.3 mg), and sodium acetate (15 mg) was stirred at room temperature for 2 hours. Then addition of 4 ml of water, extraction with ether, washing with water, drying and concentration in vacuo gave 58 mg of crude product. Purification by preparative layer silica gel chromatography with a $CH_2Cl_{12}$ MeOH 95:5 solvent mixture gave 37 mg of pure 22,23-dihydro-4"-oxo-5-O-tert-butyl-dimethyl silyl avermectin B1a/B1b semicarbazone, which was characterized by its mass and $^1$H-NMR spectra.

EXAMPLE 29

22,23-Dihydro 4"-oxo-avermectin B1a/B1b semicarbazone

A solution of 35 mg of 22,23-dihydro-4"oxo-5-O-tert butyldimethylsilyl-avermectin B1a/B1b semicarbazone in 3.5 ml of MeOH containing 1% of p-toluenesulfonic acid monohydrate was held at room temperature for 60 minutes. Addition of aqueous $NaHCO_3$ solution, extraction with ether, washing with water drying and concentration in vacuo gave 23 mg of crude product. Purification by preparative layer silica gel chromatography using a $CH_2C_{12}$-MeOH 94:6 solvent mixture afforded 5.2 mg of pure 22,23 dihydro-4"-oxo avermectin B1a/B1b semicarbazone, which was characterized by its mass and $^1$NMR spectra.

EXAMPLE 30

5-O-t-Butyldiphenylsilylavermectin B1a/B1b

A solution of 7.25 g of avermectin B1a/B1b in 50 ml of N,N-dimethylformamide was stirred with 3 ml of t-butyldiphenylsilyl chloride, 1.5 g imidazole, and 200 mg N,N-dimethylaminopyridine at room temperature for 48 hours. The reaction was stopped by addition of water, and extraction with dichloromethane afforded the product as an oil. High performance liquid chromatography (HPLC) on silica gel using 1.4:3 (v:v) ethyl acetate:hexane provided 7.7 g purified 5-O-t-butyldiphenylsilylavermectin B1a/B1b as a foam, which was characterized by its $^1$NMR spectra.

EXAMPLE 31

5-O-tert-Butyldimethylsilyl-10,11-dihydro-10-hydroxyavermectin B1a/B1b

To a solution of 500 mg of 5-O-tert butyldimethylsilyl avermectin B1a/B1b in 10 ml of acetone and 1.0 ml of water was added 110 mg of N-bromo acetamide in one portion. The mixture was stirred in the dark at 20° C. for 1 h, and work up consisted of addition of water and extraction with ether or dichloromethane. The solvent was removed in vacuo and the residual solid was purified by preparative thick layer silica gel chromatography using a 1:1 hexane:ethyl acetate solvent system to afford 180 mg of 5-O-tert butyldimethylsilyl--11-bromo 10,11-dihydro-10-hydroxyavermectin B1a/B1b. This intermediate product was dissolved in 6 ml of toluene, and 0.4 ml of tri-n-butyltin hydride was added. The mixture was heated at 100° C. under an atmosphere of nitrogen for 2 hours. Column chromatography on silica gel with dichloromethane followed by 1:1 hexane : ethyl acetate provided an initial separation of the product from the tin compounds. Final purification of the product was achieved by HPLC on a C-18 reverse phase column using a methanol water liquid phase to afford 60 mg of 5-O-tert-butyldimethylsilyl-10,11-dihydro10-hydroxy avermectin B1a/B1b which was characterized by its NMR and mass spectra.

EXAMPLE 32

5-O-tert-Butyldimethylsilyl 10,11-dihydro-10-hydroxy-4''-O-trimethylsilylavermectin B1a/B1b To 2.0 g of 5-O-tert-butyldimethylsilyl-10,11 dihydro-10-hydroxyavermectin B1a/B1b was added 20 ml of freshly distilled dichloromethane, 4 ml of (4A sieve-dried) N,N-dimethyl formamide, and 1.0 ml of freshly distilled triethylamine. To this mixture, after cooling to 0° C., was added 0.410 ml of chlorotrimethylsilane. The reaction mixture was stirred at 20° C. for 2 hours. The reaction mixture was then quenched with 300 ml of water and 60 ml of a saturated sodium bicarbonate solution. Extraction with dichloromethane and evaporation of the solvent yielded the product as a solid. Purification by chromatography on silica gel using 3:1 hexane:EtOAc afforded 1.33 of 5-O-tert-butyldimethylsilyl-10,11-dihydro-10-hydroxy-4''-O-trimethylsilylavermectin B1a/B1b which was characterized by its NMR and mass spectra.

EXAMPLE 33

5-O-tert Butyldimethylsilyl-10,11-dihydro-10-fluoroavermectin B1a/B1b

A solution of 1.68 g of 5-O-tert-butyl-dimeathylsilyl 10,11-dihydro-10-hydroxy 4''-O-trimethylsilyl-avermectin B1a/B1b in 20 ml of freshly distilled dichloromethane under nitrogen was cooled to −78° C. To this mixture was added dropwise 0.23 ml of diethylaminosulfur trifluoride. After 1 hour at 78° C. the reaction was quenched aqueous with 5 ml of a 7% sodium carbonate solution. Extraction with dichloromethane from the aqueous workup afforded 1.73 g of crude products. This mixture of products was dissolved in 20 ml of THF:water (9:1) and 125 mg of p-toluenesulfonic acid monohydrate was added in one portion. After exactly 15 min at 20° C. the reaction was quenched by addition of 5 ml of a saturated aqueous sodium bicarbonate solution. Dichloromethane extraction of the aqueous workup afforded 1.59 g of products (two major components by TLC analysis). Chromatographic purification on silica gel using hexane: ethyl acetate (2:1) afforded 781 mg of 5-O-tert-butyldimsthylsilyl-10,11-dihydro-10-fluoroavermectin B1a/B1b and 710 mg of 5-O-tert butyldimethylsilyl-10,1110-hydroxy avermectin B1a/B1b, which were characterized by their NMR and mass spectra.

EXAMPLE 34

5-O-tert-Butyldimethylsilyl-10,11-dihydro-10-fluoro-4''-oxoavermectin B1a/B1b

To 3.0 ml of freshly distilled dichloromethane at −78° C. under nitrogen was added 41 μl of DMSO and 63 μl of oxalyl chloride. After 1 min. a 1.5 ml solution of 287 mg of 5-O-tert-butyldimethylsilyl-10,11 dihydro 10-fluoroavermectin B1a/B1b in dichloromethane was added dropwise over 5 min. After 2 hours at −78° C. 0.5 ml of freshly distilled triethylamine was added dropwise to the reaction mixture. After another hour at 78° C. the reaction was worked up by the addition of 2 ml of a saturated sodium bicarbonate solution and warming to room temperature. Extraction of the product from the aqueous workup with dichloromethane and evaporation of the solvent gave the crude product as a solid. Chromatographic purification on silica gel using hexane:ethyl acetate (3:1) afforded 266 mg of 5-O-tert-butyldimethylsilyl-10,11-dihydro-10-fluoro-4''-oxoavermectin B1a/B1b which was characterized by its NMR and mass spectra.

EXAMPLE 35

5-O-tert-Butyldimethylsilyl-10,11-dihydro-10-fluoro-4''-oxoavermectin B1a/B1b toluic acid hydrazone To a solution of 50 mg (0.05 mmol) of 5-O-tert butyldimethylsily-10,11-dihydro- 10-fluoro-4''-oxoavermectin B1a/B1b in 0.5 ml of methanol was added 50 μl of -pyridine, 5 μl of acetic acid, and 10.6 mg (0.07 mmol) of p-toluic acid hydrazide. The reaction mixture was stirred at 20° C. for 18 h when thin layer chromatographic analysis (silica gel, 4% MeOH in $CH_2Cl_2$) showed the reaction to be completed. The reaction mixture was quenched with 1.0 ml of a saturated aqueous sodium bicarbonate solution, diluted with 40 ml of water, and extracted with three 15 ml portions of dichloromethane. The dichloromethane extracts were combined, dried over anhydrous sodium sulfate, and concentrated to afford the product as a solid. Final purification was achieved by preparative silica gel chromatography on plates eluted twice with 33% ethyl acetate in hexane to afford 51.3 mg of 5-O-tert butyl-dimethylsilyl-10,11-dihydro 10-fluoro-4''-oxoavermectin B1a/B1b p-toluic acid hydrazone, which was characterized by its NMR and mass spectra.

EXAMPLE 36

10,11-Dihydro-10-fluoro-4''-oxoavermectin B1a/B1b p-toluic acid hydrazone

To a solution of 51.3 mg of 5-O- tert-butyldimethylsilyl-10,11-dihydro-10-fluoro 4''-oxoavermectin B1a/B1b p-toluic acid hydrazone in 2.5 ml of freshly distilled tetrahydrofuran (THF) was added 2.5 ml of the hydrogen fluoride-pyridine THF solution (as described in Example 4). The reaction mixture was stirred under nitrogen at 20° C. for 18 h, after which 20 ml of ether was added. The mixture was transferred to a separator funnel containing ether and aqueous sodium bicarbonate. The neutralized aqueous layer was extracted with ether and the combined ether extract was dried over magnesium sulfate. The ether was then removed in vacuo to afford the product which was purified by chromatography on thick layer silica gel plates eluted twice with 60% ethyl acetate in hexane. The purified 10,11-dihydro-10-fluoro 4"-oxoavermectin B1a/B1b p-toluic acid hydrazone (31 mg) was characterized by NMR and mass spectroscopy.

EXAMPLE 37

5-O-tert-Butyldimethylsilyl-10,11-dihydro 10 fluoro-4"oxoavermectin B1a/B1b semicarbazone To a solution of 50 mg (0.05 mmol) of 5-O- tert-butyldimethylsilyl-10,11-dihydro-10-fluoro-4"-oxoavermectin B1a/B1b in 1 ml of methanol was added 50 µl of pyridine and 50 mg of semicarbazide hydrochloride. The reaction mixture was stirred at 20° C. for 18 h and then transferred to a separatory funnel containing 30 ml of water. The mixture was extracted with three 20 ml portions of ether, and the ether extracts were combined, dried over sodium sulfate, and concentrated to afford the product as a glossy solid. Initial purification was achieved by silica gel thick layer chromatography to remove the pyridine and traces of impurities (eluting 3 times with 4% methanol in dichloromethane). Final purification was accomplished by reverse phase HPLC using a C18 Whatman Partisil M20 10/50 ODS-3 column eluting with methanol-water (90:10) to afford 31 mg of 5-O-tert-butyldimethylsilyl-10,11-dihydro-10-fluoro-4"oxoavermectin B1a/B1b semicarbazone which was characterized by its NMR and mass spectra.

EXAMPLE 38

10,11 dihydro-10-fluoro-4"oxoaermectin B1a/B1b semicarbazone

The desilylation procedure given in Example 4 was followed utilizing 31 mg of 5-O-tert-butyldimethylsilyl-10,11-dihydro-10-fluoro-4"-oxoermectin B1a/b1b semicarbazone, 1.5 ml of THF, and 1.5 ml of HF-pyridine solution. The same aqueous workup, followed by chromatographic purification (silica gel TLC eluting 2 times with 1% methanol in ethyl acetate) afforded 24 mg of 10,11-dihydro-10-fluoro-4"-oxoavermectin B1a/B1b semicarbazone, which was characterized by its NMR and mass spectra.

EXAMPLE 39

5-O-tert Butyldimethylsilyl-10,11-dihydro 10-fluoro-4"'-oxoavermectin B1a/B1b 4,4-dimethylsemicarbazone The procedure outlined in Example 35 was followed using 49.6 mg of 5-O-tert-butyldimethylsilyl-10,11-dihydro-10-fluoro-4"-oxoavermectin B1b/B1b, 0.5 ml of methanol, 50 µl of pyridine, 5 µl of acetic acid, and 6.8 mg of 4,4-dimethylsemicarbazide. The same aqueous workup, followed by reverse phase HPLC purification (C18 Magnum 20 column, mobile phase methanol-water 90:10) afforded 23 mg of pure 5-O- tert-butyldimthylsilyl-10,11dihydro-10-fluoro-4"-oxoavermectin B1a/B1b 4,4-dimethylsemicarbazone, which was characterized by its NMR and mass spectra.

EXAMPLE 40

10,11-Dihydro-10-fluoro 4"'-oxoavermectin B1a/B1b 4,4-dimeathylsemicarbazone

The proceined in Example 36 was followed using 23 mg of 5-O-tert-butyldimethylsilyl-10,11 -dihydro-10-fluoro-4"-oxoavermectin B1a/B1b 4,4-dimethylsemicarbazone, 1.2 ml of THF, and 1.2 ml of HF-pyridine solution. The same aqueous workup after 18 h at 20° C., followed by silica gel TLC (2 elutions with 1% methanol in ethyl acetate) afforded 10 mg of 10,11-dihydro-10-fluoro-4"-oxoavermectin B1a/B1b 4,4-dimethylsemicarbazone, which was characterized by its NMR and mass spectra.

EXAMPLE 41

5-O-tert-Butyldimethylsilyl-10,11-dihydro-10-fluoro-4"-oxoavermectin B1a/B1b p-toluenesulfonylhydrazone The procedure outlined in Example 35 was followed using 100.3 mg of 5-O-tert-butyldimethylsilyl-10,11-dihydro-10-fluoro-4"-oxoavermeactin B1a/B1b, 1.0 ml of methanol 100 µl of pyridine, 10 µl of acetic acid, and 24.6 mg of p-toluenesulfonylhydrazine. After 18 h at 20° C., the same aqueous workup, followed by preparative silica gel TLC produced the two products A (28.3 mg) and B (56.2 mg). Compound A (RF=0.5, hexane:ethylacetate 2:1) had an NMR spectrum which was consistent with the desired product while compound B (Rf=0.45) had an NMR spectrum which indicated possible epimerization at the 3" or 5" position. Compound A was further purified by reverse phase HPLC (C18 Magnum 20 column, methanol-water 91:9) to yield 22 mg of 5-O-tert-butyl-dimethylsilyl- 10,11-dihydro-10-fluoro-4"-oxoavermectin B1a/B1b p-toluenesulfonylhydrazone, which was characterized by its mass and hu 1H-NMR spectra.

EXAMPLE 42

10,11 Dihydro-10-fluoro-4"-oxoavermectin B1a/B1b p-toluenesulfonylhydrazone

The procedure of Example 36 was followed using 22 mg of 5-O-tert butyldimethyl-silyl-10,11-dihydro-10-fluoro-4"-oxoavermectin B1a/B1b p-toluenesulfonylhydrazone, 1.1 ml of THF and 1.1 ml of HF-pyridine solution. After 18 h at 20° C., the same aqueous workup, followed by silica gel preparative TLC (1:1 hexane ethyl acetate, 2 elutions) afforded 9 mg of 10,11-dihydro-10-fluoro-4"-oxoavermectin B1a/B1b p-toluenesulfonylhydrazone, which was characterized by its NMR and mass spectra.

EXAMPLE 43

5-O-tert-Butyldimethylsilyl-4"-oxoavermectin B1a/B1b methoxime

To a solution of 100 mg of 5-O-tert-butyldimethylsilyl-4"-oxoavermectin B1a/B1b in 5 ml of methanol was added 50 mg of O-methylhydroxylamine hydrochloride and 100 microliters of pyridine. The mixture was stirred at 20° C. for 16 h. The solvent was then removed in vacuo. The residue was dissolved in dichloromethane and purified by preparative thin layer silica gel chromatography (Rf=0.75, hexane:ethylacetate 2:1) to afford 70 mg of 5-O-tert butyldimethylsilyl-4"-oxoavermectin B1a/B1b methoxime, which was characterized by its NMR and mass spectra.

EXAMPLE 44

4"Oxoavermectin B1a/B1b methoxime

To 65 mg of 5-O-tert butyldimethylsilyl-4"-oxoavermectin B1a/B1b methoxime in a polypropylene vial was added 2 ml of THF and 2 ml of hydrogen fluoride-pyridine solution according to the procedure fully described in Example 4. The reaction mixture was stirred at 20° C. for 16 h. Standard aqueous workup and preparative TLC purification afforded 55 mg of 4"-oxoavermectin B1a/B1b methoxime, which was characterized by its NMR and mass spectra.

EXAMPLE 45

5-O-tert Butyldimethylsilyl 4"-oxoavermectin B1a/B1b semicarbazone

To a solution of 200 mg of 5-O-tert-butyldimethylsilyl-4"-oxoavermectin B1a/B1b in 2 ml of methanol and 2 ml of pyridine was added 200 mg of semicarbazide hydrochloride. The mixture was stirred at 20° C. for 18 h and the solvent was removed in vacuo. The residue was purified by preparative TLC (silica gel, 4% methanol in dichloromethane) to afford 82 mg of a band with an Rf of 0.40. Further purification by reverse phase HPLC (92:8 v/v methanol:water) afforded 58 mg of pure 5-O-tert-butyldimethylsilyl-4"-oxoavermectin B1a/B1b semicarbazone, which was characterized by its NMR and mass spectra.

EXAMPLE 46

4"Oxoavermectin B1a/B1b semicarbazone

When 5-O-tert-butyldimethylsilyl-4"-oxoavermectin B1a/B1b semicarbazone was reacted according to the procedure of Example 36, 4"-oxoavermectin B1a/B1b semicarbazone was obtained as product, which was characterized by its mass and $^1$H-NMR spectra.

EXAMPLE 47

4"-Epi-(2,2-dimethylhydrazin-1-yl)-4"-deoxy-avermectin B1a/B1b 8,9-oxide

A solution of 135 mg of 4"-epi-(2,2-dimethylhydrazin-1-yl)- 4"-deoxy-avermectin B1a/B1b and 6 mg of vanadium(III) acetylacetonate in dry CH$_2$Cl$_2$ is treated with a solution of 71 μl of a 3.0 molar solution of tert butyl hydroperoxide in toluene and left at room temperature for 22 hours. Then the reaction mixture is poured into aqueous dilute sodium bicarbonate, and the product extracted with methylene chloride. The extract is washed with aqueous sodium bicarbonate solution and water, dried and evaporated in vacuo. Purification of the residue by preparative TLC on silica gel gives 4"-epi-(2,2-dimethylhydrain-1-yl)-4"-deoxy-avermeltin B1b a/B1b 8,9-oxide, which is characterized by its mass and $^1$H NMR spectra.

What is claimed is:

1. A compound having the formula:

wherein
m is 0 or 1;
R$_1$ is $$R-(X)_n-\underset{\underset{R'}{|}}{N}-N=,$$

$$R-(X)_n-\underset{\underset{R'}{|}}{N}-NH- \text{ or}$$

RON= wherein
n is 0 or 1;
R is hydrogen, amino, loweralkyl, mono- or di-lower alkyl amino, methoxy-loweralkylamino, diloweralkylaminoloweralkyl, diloweralkylaminoloweralkylamino, loweralkylphenyl, loweralkyl phenylamino, loweralkoxyphenyl, loweralkoxyphenylamino, halophenyl, halophenylamino, sulfamylphenyl, sulfamylphenylamino, morpholinyl, N-loweralkyl piperazinyl, N-(loweralkoxy phenyl)piperazinyl, N-(halophenyl)piperazinyl, benzimidazolylamino, pyrimidinylamino, thiazolylamino, benzothiazolylamino or N-(loweralkylphenyl)piperzinyl
R' is hydrogen or loweralkyl;
X is carbonyl or sulfonyl;
A is a double bond or an epoxide;
B is a single bond or a double bond;
R$_2$ is hydrogen or hydroxy,
R$_3$ is iso-propyl or sec-butyl,
R$_4$ is hydroxy or methoxy,
R$_5$ and R$_6$ are present only when B is a single bond and are independently hydrogen, hydroxy or halogen;
and the broken line indicates a single or a double bond at the 22,23-position, provided that R$_2$ is hydroxy only when the broken line indicates a single bond.

2. The compound of claim 1 wherein $R_1$ is

and R is, amino, loweralkyl, mono- or di-lower alkyl amino, methoxy-loweralkylamino, diloweralkylaminolo-weralkylamino, loweralkylphenyl, loweralkyl -phenylamino, halophenyl, halophenylamino, morpholinyl, N-loweralkyl piperazinyl, N-(loweralkoxyphenyl)-piperazinyl, N-(halophenyl)piperazinyl, or N-(loweralkyl phenyl) piperazinyl;

or $R_1$ is

—NH—NRR' and R is, loweralkyl, methoxyloweralkyl, diloweralkylamino loweralkyl, loweralkylphenyl, halophenyl, morpholinyl carbonyl, N-loweralkyl piperazinylcarbonyl, or N-(loweralkylphenyl)-piperazinylcarbonyl;

$R^1$ is a hydrogen or loweralkyl;
A is a double bond
B is a single bond or a double bond;
$R_2$ is hydrogen
$R_3$ is iso-propyl or sec-butyl,
$R_4$ is hydroxy
$R_5$ and $R_6$ are present only when B is a single bond and are independently hydrogen or fluorine.
and the broken line indicates a single or a double bond at the 22,23-position.

3. The compound of claim 2 wherein
m=1
$R_1$ is

and R is, mono- or di-loweralkylamino, diloweralkylamino-, loweralkylamino, loweralkylphenyl, halophenyl, N-loweralkyl piperazinyl or N (loweralkylphenyl) piperazinyl;

or $R_1$ is

—NH—NRR' and R is loweralkyl, or N-(loweralkylphenyl)-piperazinyl;
R' is hydrogen or loweralkyl;
A is a double bond
B is a double bond;
$R_2$ is hydrogen;
$R_3$ is iso-propyl or sec-butyl,
$R_4$ is hydroxy;
$R_5$ and $R_6$ are hydrogen;
and the broken line indicates a single or a double bond at the 22,23-position.

4. The compound of claim 3 which is 4'''-Oxoavermectin B1a/B1b 4,4-dimethylsemicarbazone.

5. The compound of claim 2 which is 10,11-Dihydro-10-fluoro-4''-oxoavermectin B1a/B1b-semicarbazone.

6. The compound of claim 3 which is 4-'''-Oxoavermectin B1a/B1b 2-[4-(4-chlorophenyl)piperazin-1-yl)carbonyl]hydrazone.

7. The compound of claim 3 which is 4'''-Oxoavermectin B1a/B1b 2-{[4-(4-tolyl)piperazin-1-yl]carbonyl} hydrazone.

8. The compound of claim 3 which is 4''-epi-(2,2-Dimethylhydrazin-1-yl) 4''-deoxyavermectin B1a/B1b.

9. The compound of claim 3 which is 22,23-Dihydro-4''-epi-(2,2-dimethylhydrazin-1-yl) 4''-deoxyavermectin B1a/B1b.

10. The compound of claim 1 which is 22,23-Dihydro-4'-epi-(2,2-dimethylhydrazin-1-yl)-4'-deoxyavermectin B1a/B1b monosaccharide.

11. A method for the treatment of parasitic infections which comprises administering to an animal infected with parasites an effective amount of a compound of claim 1.

12. A method for the treatment of parasitic infestations of agricultural crops which comprises treating such crops while they are growing or while in storage with an effective amount of a compound of claim 1.

13. A composition useful for treating animals infected with parasites or areas infested with parasites which comprises an inert carrier and an effective amount of a compound of claim 1.

* * * * *